US00PP13307P3

(12) United States Plant Patent
Davino, Jr.

(10) Patent No.: US PP13,307 P3
(45) Date of Patent: Dec. 3, 2002

(54) CHRYSANTHEMUM PLANT NAMED 'ZESTY YOMEGAN'

(75) Inventor: Louis Davino, Jr., Hightstown, NJ (US)

(73) Assignee: Yoder Brothers, Inc., Barberton, OH (US)

( * ) Notice: Subject to any disclaimer, the term of this patent is extended or adjusted under 35 U.S.C. 154(b) by 37 days.

(21) Appl. No.: 09/837,577

(22) Filed: Apr. 19, 2001

(65) Prior Publication Data

US 2002/0157154 P1 Oct. 24, 2002

(51) Int. Cl.[7] ..... A01H 5/00

(52) U.S. Cl. ..... Plt./286

(58) Field of Search ..... Plt./286, 287, 291, Plt./292, 297

*Primary Examiner*—Howard J. Locker

(74) *Attorney, Agent, or Firm*—C. A. Whealy

(57) ABSTRACT

A distinct cultivar of Chrysanthemum plant named 'Zesty Yomegan', characterized by its upright plant habit; freely branching growth habit; uniform and freely flowering habit; duplex daisy-type inflorescences; and dark pink-colored ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Zesty Yomegan'.

The new Chrysanthemum is a naturally-occurring whole plant mutation of the Chrysanthemum cultivar Megan, disclosed in U.S. Plant Pat. No. 8,756. The new Chrysanthemum was discovered and selected by the Inventor as a single flowering plant within a population of flowering plants of the parent cultivar in October, 1996 in a controlled environment in Highstown, N.J. The selection of this plant was based on its unique ray floret color.

Asexual reproduction of the new cultivar by terminal cuttings taken in a controlled environment in Gainesville, Fla. since December, 1997, has shown that the unique features of this new Chrysanthemum are stable and reproduced true to type in successive generations.

SUMMARY OF THE INVENTION

The cultivar Zesty Yomegan has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zesty Yomegan'. These characteristics in combination distinguish 'Zesty Yomegan' as a new and distinct cultivar:

1. Upright plant habit.
2. Freely branching, dense, full plants.
3. Uniform and freely flowering.
4. Duplex daisy-type inflorescences.
5. Dark pink-colored ray florets.

Compared to plants of the parent cultivar Megan, plants of the new Chrysanthemum flower earlier and differ in ray floret color.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Zesty Yomegan'.

The photograph at the bottom of the sheet comprises a close-up view of typical inflorescences of the cultivar 'Zesty Yomegan'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Zesty Yomegan.

Commercial classification: Duplex daisy-type garden Chrysanthemum.

Parentage: Naturally-occurring whole plant mutation of *Chrysanthemum×morifolium* cultivar Megan, disclosed in U.S. Plant Pat. No. 8,756.

Propagation:

*Type*.—Terminal tip cuttings.

*Time to initiate roots*.—About four days at 21° C.

*Time to produce a rooted cutting*.—About ten days at 21° C.

*Root description*.—White, fine and fibrous.

*Rooting habit*.—Freely branching.

Plant description:

*Appearance*.—Perennial herbaceous duplex daisy-type garden Chrysanthemum. Inverted triangle; upright plant form. Stems initially upright, then slightly outwardly spreading giving a uniformly flat-top to mounded appearance to the plant. Freely branching with about 10 lateral branches per plant.

*Plant height*.—About 30 cm.

*Plant diameter*.—About 33 cm.

*Lateral branches*.—Length: About 25 cm. Diameter: About 5 mm. Internode length: About 2.2 cm. Aspect: Mostly upright. Texture: Pubescent. Color: 144A overlain with anthocyanin, close to 59A.

*Foliage description*.—Leaf arrangement: Alternate. Length: About 3.4 cm. Width: About 2.8 cm. Apex: Cuspidate to mucronate. Base: Attenuate to truncate. Margin: Palmately lobed, sinuses mostly divergent. Texture: Both surfaces, pubescent; veins prominent on lower surface. Color: Young foliage upper surface: 147 A. Young foliage lower surface: 147 B. Mature foliage upper surface: 147 A. Mature foliage lower surface: 147 B. Venation, both surfaces: 146 B. Petiole length: About 1.7 cm. Petiole diameter: About 2 mm. Petiole color, both surfaces: 146B to 146C.

Inflorescence description:

*Appearance*.—Duplex daisy-type inflorescence form with elongated oblong-shaped ray florets. Inflorescences borne on terminals above foliage, arising from leaf axils. Disk and ray florets arranged acropetally on a capitulum. About 9 inflorescences per lateral; about 90 inflorescences per plant.

*Flowering response*.—Under natural season conditions, plants flower in late September to early October in the Northern Hemisphere and continue to flower for at least three weeks depending on weather conditions.

*Inflorescence bud* (*before showing color*).—Height: About 5 mm. Diameter: About 7 mm. Phyllary color: 143A.

*Inflorescence size*.—Diameter: About 5 cm. Depth (height): About 1.3 cm. Disc diameter: About 9 mm. Receptacle diameter: About 4.5 mm.

*Ray florets*.—Shape: Elongated oblong. Length: About 2.4 cm. Corolla tube length: About 3.5 mm. Width: About 5 mm. Apex: Acute, emarginate or dentate. Margin: Entire. Texture: Smooth, glabrous, satiny. Orientation: Initially upright then perpendicular to the peduncle; mostly flat to slightly convex with development. Number of ray florets per inflorescence: About 110 in about six rows. Color: When opening, upper surface: Close to 186A faintly overlain with 71A. When opening, lower surface: Close to 186A. Opened inflorescence, upper surface: Close to 186A faintly overlain with 71A. Opened inflorescence, lower surface: Close to 186A to 186B.

*Disc florets*.—Shape: Tubular, apex dentate. Length: About 6 mm. Width: Apex: About 1.5 mm. Base: About 1 mm. Number of disc florets per inflorescence: About 30. Color: Immature: 154A. Mature: Apex: 9A. Mid-section: 154D. Base: 155D.

*Peduncle*.—Aspect: Flexible, angled about 40° from the stem. Length: First peduncle: About 6.1 cm. Fourth peduncle: About 9.4 cm. Diameter: About 2 mm. Texture: Pubescent. Color: Close to 146A.

*Reproductive organs*.—Androecium: Present on disc florets only. Anther color: 9A. Pollen: None. Gynoecium: Present on both ray and disc florets.

*Seed*.—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to rain and wind.

It is claimed:

1. A new and distinct cultivar of Chrysanthemum plant named 'Zesty Yomegan', as illustrated and described.

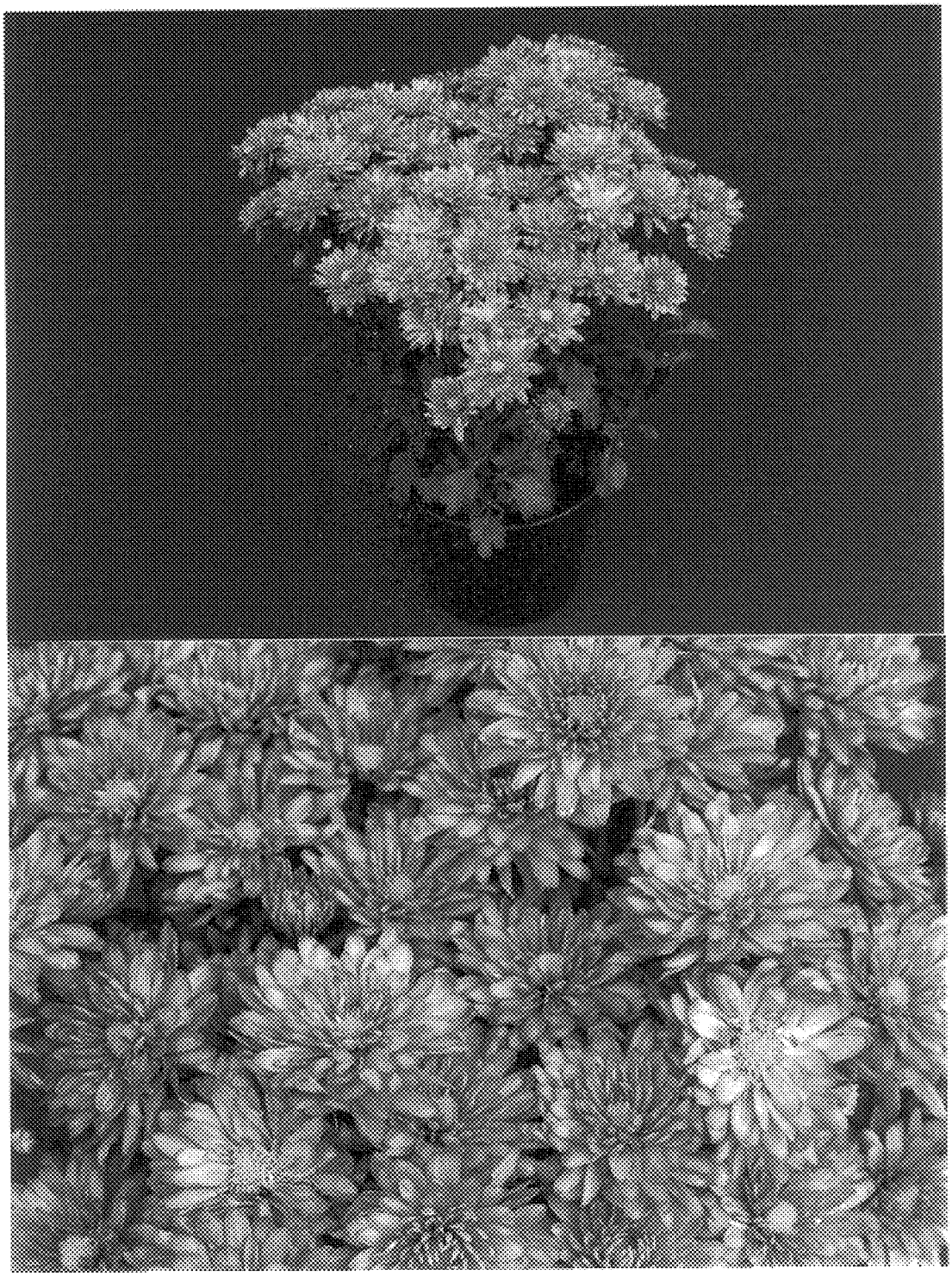

* * * * *